United States Patent
Liu et al.

(10) Patent No.: US 11,884,991 B2
(45) Date of Patent: Jan. 30, 2024

(54) METHOD FOR INCREASING THE STRAIGHTNESS OF A THIN WIRE

(71) Applicant: Heraeus Materials Singapore Pte., Ltd., Singapore (SG)

(72) Inventors: Zhen Yun Liu, Singapore (SG); Muhammad Shahzali Bin Jolani, Singapore (SG); Yang Yu, Singapore (SG)

(73) Assignee: Heraeus Materials Singapore Pte., Ltd., Singapore (SG)

( * ) Notice: Subject to any disclaimer, the term of this patent is extended or adjusted under 35 U.S.C. 154(b) by 120 days.

(21) Appl. No.: 17/213,881

(22) Filed: Mar. 26, 2021

(65) Prior Publication Data
US 2021/0301366 A1 Sep. 30, 2021

(30) Foreign Application Priority Data
Mar. 27, 2020 (EP) ..................... 20166511

(51) Int. Cl.
| C21D 9/52 | (2006.01) |
|---|---|
| C21D 1/26 | (2006.01) |
| C21D 8/06 | (2006.01) |
| B21F 1/02 | (2006.01) |
| C21D 1/84 | (2006.01) |

(52) U.S. Cl.
CPC .............. *C21D 9/52* (2013.01); *B21F 1/02* (2013.01); *C21D 1/26* (2013.01); *C21D 1/84* (2013.01); *C21D 8/06* (2013.01); *C21D 9/525* (2013.01)

(58) Field of Classification Search
CPC .............. C21D 8/06; C21D 9/525; B21F 1/02
See application file for complete search history.

(56) References Cited

U.S. PATENT DOCUMENTS

| 2002/0174922 A1* | 11/2002 | Ishii ................ A61L 29/02 148/407 |
| 2016/0151610 A1* | 6/2016 | Schaffer ........... C21D 1/26 148/563 |
| 2017/0101697 A1* | 4/2017 | Honkura ........... C21D 9/564 |
| 2019/0261511 A1 | 8/2019 | Frick et al. |

FOREIGN PATENT DOCUMENTS

| CN | 105 154 657 | 12/2015 |
| CN | 104114123 B * | 5/2017 ............ A61C 5/42 |
| CN | 108 823 369 | 11/2018 |
| CN | 208 667 797 | 3/2019 |
| CN | 110 814 072 | 2/2020 |
| JP | 10306358 A * | 11/1998 |

OTHER PUBLICATIONS

Wright, Robert Wire Technology—Process Engineering and Metallurgy, 9.7 Drawing Practice and Cast and Pitch Control, Drawing Die and Pass Schedule Design, p. 109, May 2016.
Wright, Robert Wire Technology—Process Engineering and Metallurgy, 11.3.5 Anneling, Wire Technology, p. 142, May 2016.

* cited by examiner

*Primary Examiner* — Sally A Merkling
*Assistant Examiner* — Sean P. O'Keefe
(74) *Attorney, Agent, or Firm* — Dicke, Billig & Czaja, PLLC

(57) ABSTRACT

A method for producing a further wire, wherein the method includes, providing a first wire and feeding the first wire through a furnace to obtain the further wire. A further cast of the further wire is larger than a first cast of the first wire.

8 Claims, 7 Drawing Sheets

100

Fig. 4A            400
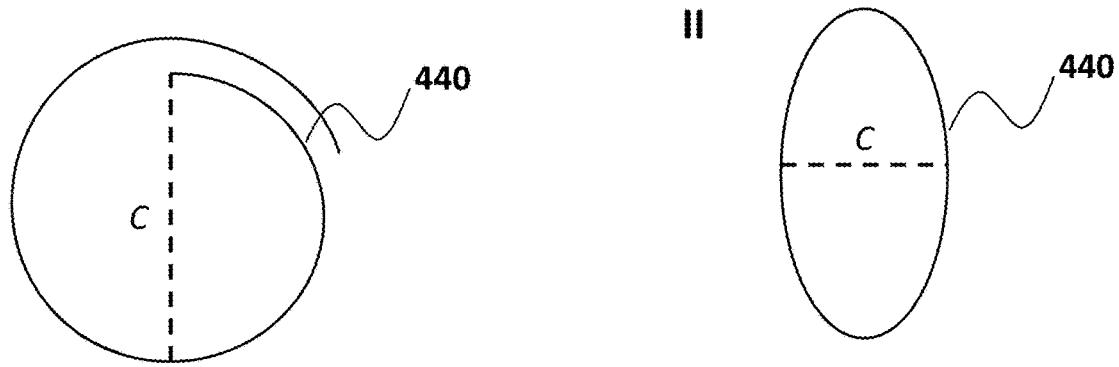
Fig. 4B
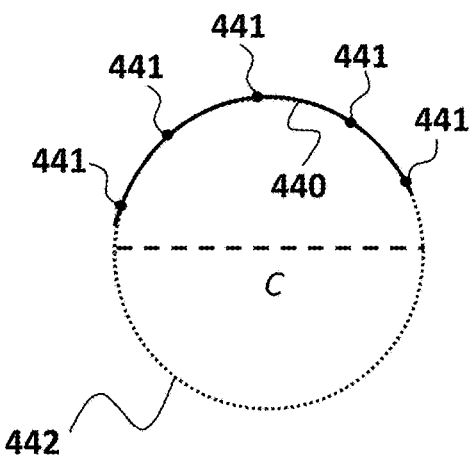
Fig. 4C
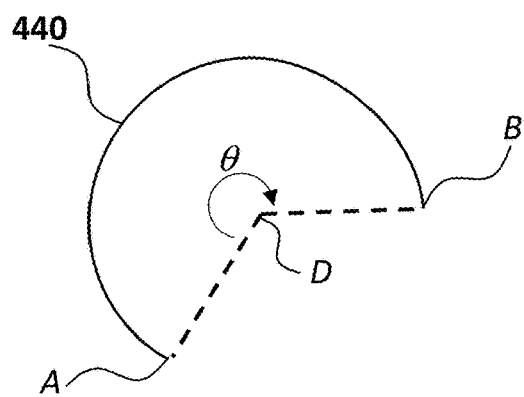

METHOD FOR INCREASING THE STRAIGHTNESS OF A THIN WIRE

CROSS-REFERENCE TO RELATED APPLICATION

This Utility Patent Application claims priority to European Patent Application No. 20166511.4, filed Mar. 27, 2020, which is incorporated herein by reference.

FIELD OF THE INVENTION

In general, one aspect relates to the production of thin wires. One aspect relates to a method for straightening the wires. One aspect further relates to the wires that are obtained by the aforementioned method.

BACKGROUND

Thin wires segments are often used as components in sensitive measuring equipment, as well as components in medical devices. These thin wire segments have a diameter that is less than 0.5 mm. A particular example is using the wire segments as sensors for continuous glucose monitoring devices. In order to ensure that, e.g., the measuring equipment provide accurate measurements, or that the medical devices are reliable, it is required that the wire segments are defect-free. In order to produce defect-free wire segments from a wire, numerous steps in a production process of the wire require that the wire should have a large cast, where cast is a measure of the "straightness" of the wire.

The cast of the wire is generally increased using mechanical means, i.e., using a straightening device to apply at least one external force to the wire. A first example is the straightening device disclosed in CN 105 154 657. The straightening device includes a plurality of rollers, wherein the rollers are arranged in two rows. The wire is then fed between the two rows of rollers, with the rollers exerting a compressive force on the wire.

In CN 105 154 657, the force applied by the rollers on the wire leads to the wire being damaged, e.g., scratches on a surface of the wire. The application of the force also leads to a change in a diameter of the wire. While such a change in diameter is in general not a problem for wires with a diameter of a few mm, such a change in diameter is very problematic for wires with a diameter of less than 0.5 mm. The rollers also increase the production costs as multiple sets of rollers are generally needed to increase the cast of the wire. Furthermore, the rollers often get jammed due to particles getting stuck between the rollers. This leads to longer downtime for repair and maintenance. The rollers also require more time to set-up for every new wire that has to be straightened.

A second example is the straightening device disclosed in CN 208 667 797 U. CN 208 667 797 U provides an inline annealing and straightening device that can handle multiple wires. Here, the straightening device includes a plurality of first winches and further winches. A plurality of titanium-nickel alloy wires, with a diameter of 0.6 mm or larger, are initially arranged around the first winches. In a subsequent step, the first winches pay out the wires, while the further winches take up the wires. The cast of the wires can be increased by varying the tension, as well as the pay-out/take-up speeds. However, this document also does not address the increase in the cast of a wire that can be obtained.

In CN 208 667 797 U, if the tension in the wire is too large, this leads to a decrease in the diameter of the wire, or often to the wire breaking. This is especially a problem for wires with a diameter of less than 0.5 mm. As the tension in the wire has to be controlled very carefully, this requires that the plurality of first winches and further winches have to function almost perfectly. E.g., if the further winch rotates only marginally slower than the required speed, this leads to a decrease in the tension of the wire, thereby making it very difficult to obtain an increase in the cast of the wire. Therefore, CN 208 667 797 U requires longer downtime for maintenance. It is also complicated to set-up CN 208 667 797 U, as each pair of first winch and further winch is operated independent from the other first winches and further winches.

The above-mentioned methods therefore have the disadvantage that the wire is often damaged, e.g., a surface of the wire is scratched, during the straightening process, and that the diameter of the wire is changed. Wire segments for medical devices must be free of damage and must have a consistent diameter. It is therefore difficult to produce the wire segments from the wires that have been produced using the above-mentioned embodiments.

Additionally, the methods are often slow, thereby limiting the wire production efficiency. Furthermore, apart from the equipment used for producing the wire, the additional equipment required for straightening the wire increases costs. The requirement for additional equipment not only increases production costs, but also increases the complexity of the production equipment. For these and other reasons there is a need for the present embodiment.

SUMMARY

An object of one embodiment is to at least partially overcome at least one of the disadvantages encountered in the state of the art.

It is a further object of one embodiment to provide a method for increasing the cast of a thin wire.

It is a further object of one embodiment to provide a method for increasing the cast of a thin wire that has an increased production efficiency.

It is a further object of one embodiment to provide a method for increasing the cast of a thin wire that does not damage the wire.

It is a further object of one embodiment to provide a method for increasing the cast of a thin wire that does not lead to a change in the diameter of the thin wire.

It is a further object of one embodiment to provide a method for increasing the cast of a thin wire that reduced production costs.

It is a further object of one embodiment to provide a method for increasing the cast of a thin wire that reduced the downtime of the equipment used for increasing the cast.

It is a further object of one embodiment to provide a method for increasing the cast of a thin wire that requires less set-up time in order to start performing the method.

It is a further object of one embodiment to provide a method for producing wire segments, wherein the method has an increased production efficiency for the wire segments.

It is a further object of one embodiment to provide a method for producing wire segments, wherein the method reduces the costs for producing the wire segments.

It is a further object of one embodiment to obtain wire segments from the thin wire with an increased cast.

It is a further object of one embodiment to obtain wire segments that provide more consistent measurements when these wire segments are comprised in measuring devices.

It is a further object of one embodiment to obtain wire segments that produce less noise.

BRIEF DESCRIPTION OF THE DRAWINGS

The accompanying drawings are included to provide a further understanding of embodiments and are incorporated in and constitute a part of this specification. The drawings illustrate embodiments and non-limiting examples and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

Note that the figures are not drawn to scale.

FIGS. 4A-4C: illustration of how the cast of the wire is measured.

DETAILED DESCRIPTION

Figure 1:
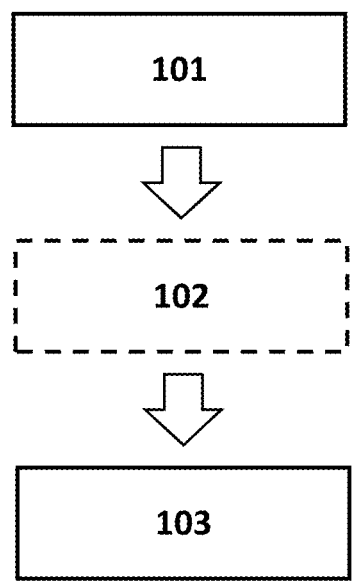
FIG. 1: flowchart illustrating the comprising method steps, according to the embodiment, for producing a further wire.

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense, and the scope of the present disclosure is defined by the appended claims. It is to be understood that features of the various examples described herein may be combined, in part or whole, with each other, unless specifically noted otherwise.

A contribution to at least partially fulfilling at least one of the above-mentioned objects is made by the independent embodiments. The dependent embodiments provide preferred embodiments which contribute to at least partially fulfilling at least one of the objects.

|1| A method for producing a further wire, wherein the method includes the steps of
  a. providing a first wire;
  b. feeding the first wire through a furnace to obtain the further wire;
  wherein
    a further cast of the further wire is larger than a first cast of the first wire.

|2| The method according to embodiment |1|, wherein the further cast of the further wire is larger than the first cast of the first wire by at least 150%, in one embodiment by at least 300%, in one embodiment by at least 500%, and in one embodiment by at least 1000%.

|3| The method according to any of the preceding embodiments, wherein a temperature of the furnace is in the range of 500° C. to 950° C., in one embodiment in the range of 550° C. to 800° C., in one embodiment in the range of 600° C. to 780° C., further in one embodiment in the range of 650° C. to 750° C., and even further in one embodiment in the range of 650° C. to 720° C.

|4| The method according to any of the preceding embodiments, wherein at least one or all of the following applies to the temperature of the furnace:
  a. the temperature is lower than a melting point of the first wire, in one embodiment lower by at least 500° C., in one embodiment by at least 750° C., and further in one embodiment by at least 1000° C.;
  b. the temperature is higher than a recrystallisation temperature of the first wire, in one embodiment higher by at least 50° C., in one embodiment higher by at least 100° C., and further in one embodiment by at least 200° C.

For embodiment |4|, all possible combination of the features a. and b. are embodiments. These combinations are e.g., a; b; a, b;

|5| The method according to any of the preceding embodiments, wherein the speed of feeding the first wire through the furnace is in the range of 2 m/min to 22 m/min, in one embodiment in the range of 5 m/min to 20 m/min, and in one embodiment in the range of 8 m/min to 17 m/min.

|6| The method according to any of the preceding embodiments, wherein a first section of the first wire has a residence time in the furnace that is in the range of 0.5 sec to 40 sec, in one embodiment in the range of 1.5 sec to 20 sec, and in one embodiment in the range of 3 sec to 9 sec.

|7| The method according to any of the preceding embodiments, wherein the tension on the first wire is in the range of 70 g to 200 g, in one embodiment in the range of 85 g to 150 g, and in one embodiment in the range of 100 g to 120 g.

|8| The method according to any of the preceding embodiments, wherein the further wire is fed through a cooling means.

|9| The method according to any of the preceding embodiments, wherein an average further grain size of the crystals in the further wire is larger than an average first grain size of the crystals in the first wire by at least 50%, in one embodiment by at least 80%, and in one embodiment by at least 110%.

|10| The method according to any of the preceding embodiments, wherein the first wire, the further wire, or both, includes a metal or a metal alloy, in one embodiment a metal selected from the group consisting of iridium, gold, nickel, niobium, palladium, platinum, silver, titanium, tantalum, tungsten or a combination of two or more thereof. It is also preferred that at least one of the metals forming part of the metal alloy is selected from the aforementioned group of metals.

In one embodiment, as for example in embodiment |10|, it is less preferred that the first wire, the further wire, or both, comprise a titanium-nickel alloy.

|11| The method according to any of the preceding embodiments wherein the first wire, the further wire, or both, comprise at least two layers, in one embodiment a first core layer surrounded by a further core layer, the first core layer in one embodiment including tantalum, and the further core layer further in one embodiment including platinum.

|12| The method according to any of the preceding embodiments, wherein at least one or all of the following applies to the further wire:
  a. a further cast that is larger than 300 mm, in one embodiment larger than 500 mm, and in one embodiment larger than 1000 mm;
  b. includes a first core layer, wherein the average further grain size of the first core layer is in the range of 130 nm to 480 nm, in one embodiment in the range of 150 nm to 450 nm, and in one embodiment in the range of 165 nm to 435 nm;
  c. includes a further core layer, wherein the average further grain size of the further core layer is in the range of 0.6 µm to 20 µm, in one embodiment in the range of 1.0 µm to 16 µm, and in one embodiment in the range of 2.5 µm to 14 µm;
  d. has a further ultimate tensile strength that is in the range of 1200 MPa to 2000 MPa, in one embodiment in the range of in the range of 1300 MPa to 1800 MPa, and further in one embodiment in the range of in the range of 1450 MPa to 1740 MPa.

For embodiment |12|, all possible combination of the features a. to d. are preferred embodiments. These combinations are e.g., a; b; c; d; a, b; a, c; a, d; b, c; b, d; c, d; a, b, c; a, b, d; a, c, d; b, c, d; a, b, c, d.

|13| The method according to any of the preceding embodiments, wherein at least one or all of the following applies to the first wire:
  a. a first cast that is in the range of 20 mm to 300 mm, in one embodiment in the range of 40 mm to 260 mm, and in one embodiment in the range of 60 mm to 230 mm;
  b. includes a first core layer, wherein the average further grain size of the first core layer is in the range of 20 nm to 400 nm, in one embodiment in the range of 30 nm to 350 nm, and in one embodiment in the range of 58 nm to 292 nm;
  c. includes a further core layer, wherein the average further grain size of the further core layer is in the range of 0.1 µm to 10 µm, in one embodiment in the range of 0.2 µm to 3 µm, and in one embodiment in the range of 0.4 µm to 1.8 µm;
  d. has a first ultimate tensile strength that is in the range of 1000 MPa to 1800 MPa, in one embodiment in the range of in the range of 1100 MPa to 1740 MPa, and further in one embodiment in the range of in the range of 1400 MPa to 1715 MPa.

For embodiment |13|, all possible combination of the features a. to d. are preferred embodiments. These combinations are e.g., a; b; c; d; a, b; a, c; a, d; b, c; b, d; c, d; a, b, c; a, b, d; a, c, d; b, c, d; a, b, c, d.

|14| The method according to any of the preceding embodiments, wherein at least one or all of the following applies to the first wire, the further wire, or both:
  a. a length in the range of 1000 m to 12000 m, in one embodiment in the range of 2000 m to 8000 m, and in one embodiment in the range of 3500 m to 6500 m;
  b. a diameter in the range of 40 µm to 160 µm, in one embodiment in the range of 60 µm to 140 µm, and in one embodiment in the range of 80 µm to 120 µm;
  c. an electrical conductivity in the range of $10^4$ S/m to $10^8$ S/m, in one embodiment in the range of $10^5$ S/m to $5 \times 10^7$ S/m, and in one embodiment in the range of $5 \times 10^5$ S/m to $2 \times 10^7$ S/m;
  d. a Young's modulus in the range of 10 GPa to 300 GPa, in one embodiment in the range of 70 GPa to 270 GPa, and in one embodiment in the range of 130 GPa to 240 GPa.

For embodiment |14|, all possible combination of the features a. to d. are preferred embodiments. These combinations are e.g., a; b; c; d; a, b; a, c; a, d; b, c; b, d; c, d; a, b, c; a, b, d; a, c, d; b, c, d; a, b, c, d.

|15| The method according to any of the preceding embodiments, wherein the furnace includes an inert gas, in one embodiment an inert gas selected from the group consisting of nitrogen, argon, hydrogen, or combinations of at least two or more thereof.

|16| The method according to any of the preceding embodiments, wherein the first wire, prior to being fed through the first furnace, is subjected to at least one or all of the following:
  a. a wire drawing step;
  b. a respooling step;
  c. a cleaning step.

For embodiment 1161, all possible combination of the features a. to c. are preferred embodiments. These combinations are e.g., a; b; c; a, b; a, c; b, c; a, b, c.

|17| The method according to any of the preceding embodiments, wherein the first cast, the further cast, or both, are increased using mechanical means.

|18| A further wire obtainable by the method according to any of the embodiments |1| to |17|

|19| The further wire according to embodiment |18|, wherein the further wire includes a metal or a metal alloy, in one embodiment a metal selected from the group consisting of iridium, gold, nickel, niobium, palladium, platinum, silver, titanium, tantalum, tungsten, or a combination of two or more thereof. It is also preferred that at least one of the metals forming part of the metal alloy is selected from the aforementioned group of metals.

In one embodiment, as for example in embodiment |19|, it is less preferred that the first wire, the further wire, or both, comprise a titanium-nickel alloy.

|20| The further wire according to any of the embodiments |18| to |19|, wherein the further wire includes at least two layers, in one embodiment a first core layer surrounded by a further core layer, the first core layer in one embodiment including tantalum, and the further core layer further in one embodiment including platinum.

|21| The further wire according to any of the embodiments |18| to |20|, wherein at least one or all of the following applies:
  a. includes a first core layer, wherein the average further grain size of the first core layer is in the range of 130 nm to 480 nm, in one embodiment in the range of 150 nm to 450 nm, and in one embodiment in the range of 165 nm to 435 nm;
  b. includes a further core layer, wherein the average further grain size of the further core layer is in the range of 0.6 µm to 20 µm, in one embodiment in the range of 1.0 µm to 16 µm, and in one embodiment in the range of 1.5 µm to 14 µm.

For embodiment |21|, all possible combination of the features a. to b. are preferred embodiments. These combinations are e.g., a; b; a, b.

|22| The further wire according to any of the embodiments |18| to |21|, wherein at least one or all of the following applies:
   a. a length in the range of 1000 m to 12000 m, in one embodiment in the range of 2000 m to 8000 m, and in one embodiment in the range of 3500 m to 6500 m;
   b. a diameter in the range of 40 µm to 160 µm, in one embodiment in the range of 60 µm to 140 µm, and in one embodiment in the range of 80 µm to 120 µm;
   c. an electrical conductivity in the range of $10^4$ S/m to $10^8$ S/m, in one embodiment in the range of $10^5$ S/m to $5\times10^7$ S/m, and in one embodiment in the range of $5\times10^5$ S/m to $2\times10^7$ S/m;
   d. a Young's modulus in the range of 10 GPa to 300 GPa, in one embodiment in the range of 70 GPa to 270 GPa, and in one embodiment in the range of 130 GPa to 240 GPa;
   e. a further ultimate tensile strength that is in the range of 1200 MPa to 2000 MPa, in one embodiment in the range of in the range of 1300 MPa to 1800 MPa, and further in one embodiment in the range of in the range of 1450 MPa to 1740 MPa.

For embodiment |22|, all possible combination of the features a. to e. are preferred embodiments. These combinations are e.g., a; b; c; d; e; a, b; a, c; a, d; a, e; b, c; b, d; b, e; c, d; c, e; d, e; a, b, c; a, b, d; a, b, e; a, c, d; a, c, e; a, d, e; b, c, d; b, c, e; b, d, e; c, d, e; a, b, c, d; a, b, c, e; a, b, d, e; a, c, d, e; b, c, d, e; a, b, c, d, e.

|23| A method for producing at least one wire segment, including the steps of
   a. providing a further wire according to any of the embodiments |18| to |22|;
   b. reducing a length of the further wire, in one embodiment by cutting the further wire, to obtain at least one wire segment.

|24| The at least one wire segment obtainable according to embodiment |23|.

|25| A use of the at least one wire segment according to embodiment |24| in a medical device, in one embodiment a medical device used for measuring, and in one embodiment a continuous glucose monitor.

|26| A use of the at least one wire segment according to embodiment |24| as a sensor for a medical device, in one embodiment a sensor for measuring, and in one embodiment a sensor for a continuous glucose monitor.

A first aspect of the one embodiment relates to feeding a first wire through a furnace to obtain a further wire. In the context of the present embodiment, the "further wire" is defined as any section of the "first wire" that has exited the furnace. In the context of the embodiment, it is preferred that the first wire, the further wire, or both, are a thin wire. A "thin" wire is defined as a wire with a diameter that is less than 0.5 mm. It is further preferred that the diameter of the first wire, the further wire, or both are larger than 20 µm.

The "cast" of a wire is defined as the tendency of an unconstrained wire to bend along a length of the wire. The wire is defined as being unconstrained if the wire is not held by a device or a person. E.g., an unconstrained wire is placed on a flat surface, and the wire forms a partial loop. In the context of the present embodiments, it is preferred that the cast of the wire, e.g., the first wire, is increased by using thermal means, e.g., feeding the wire through the furnace.

The Furnace

In one aspect of one embodiment, it is preferred that the furnace has a length that is in the range of 0.5 m to 2.5 m, in one embodiment in the range of 1.0 m to 2 m, and further in one embodiment in the range of 1.3 m to 1.7 m. In another aspect of one embodiment, it is preferred that the furnace is arranged and adapted for annealing the wire. Furnaces suited to the objects of one embodiment are well-known in industry, and are commercially available from e.g., Nabertherm GmbH, Germany. It is also preferred that a section of the first wire that is located inside the furnace is in thermal equilibrium with an inner volume of the furnace.

In one embodiment, the first wire includes a first core layer surrounded by a further core layer. In this embodiment it is further preferred that the temperature of the furnace is below the melting point of at least one of the core layers, in one embodiment both core layers. It is also preferred that the temperature of the furnace is above the recrystallisation temperature of at least the surface layers.

Pay-Out/Take-Up Means

In a related aspect, it is preferred that that the first wire is arranged on at least one payout means. In a further aspect it is preferred that the further wire is arranged on at least one take-up means. Here a "pay-out means" is defined as a means that is arranged and adapted to pay out a wire, while a "take-up means" is defined as a means that is arranged and adapted to take up a wire. In these aspects it is preferred in one embodiment that the at least one pay-out means, the at least one take-up means, or both, comprise at least one winch.

In a further related embodiment, it is preferred that the first wire, the further wire, or both, are arranged on at least one tension control means. Here a "tension control means" is defined as a means that is adapted and arranged to control a tension in a wire. It is also preferred that a first tension in the first wire deviates by less than 10%, in one embodiment by less than 5%, and further in one embodiment by less than 1.5% from a further tension in the further wire.

In another related embodiment, it is preferred that the first wire, the further wire, or both, are arranged on at least one support means. Here a "support means" is defined as a means that is adapted and arranged to support a wire. E.g., the support means is used to keep the further wire at a certain height. E.g., the cooling means includes a pipe through which the further wire passes. The support means is used to prevent the further wire from touching the sides of the pipe.

In yet another related embodiment, it is preferred that the first wire, the further wire, or both, are arranged on at least one guidance means. Here a "guidance means" is defined as a means that is adapted and arranged to guide a wire. E.g., the first wire is moving in a first direction. The guidance means is used to change the direction of motion of the first wire so that the first wire is moving a further direction.

In the above embodiments, it is preferred that at least one or all of the following comprise at least one pulley: at least one tension control means, at least one support means, at least one guidance means. It is preferred in one embodiment that at least one or all of the following is used to feed the first wire trough the furnace: the at least one pay-out means, the at least one take-up means, the at least one tension control means, the at least one support means, and the at least one guidance means. It is also particularly preferred that at least one or all of the following is used to obtain the further wire: the at least one pay-out means, the at least one takeup means, the at least one tension control means, the at least one support means, and the at least one guidance means.

The at least one pay-out means, the at least one take-up means, the at least one tension control means, the at least one support means, and the at least one guidance means are well-known to a person skilled in the art. A furnace comprising at least one of the aforementioned means is commercially available from Nabertherm GmbH, Germany.

Increasing Cast by Mechanical Means

In a first aspect of one embodiment, the further wire with a further cast is obtained by feeding the first wire with the first cast through the furnace. Furthermore, the further cast is larger than the first cast. Along with obtaining an increase in cast by feeding the first wire through the furnace, it is also preferred in the one embodiment to additionally increase the first cast, the further cast, or both, by mechanical means. Mechanical means increases the cast of a wire by applying a force to the wire. Mechanical means can include, e.g., passing the first wire between two sets of rollers, or by varying the further tension in the further wire. It is, however, particularly preferred to increase the cast of the first wire, the further wire, or both, without using mechanical means.

In the context of one embodiment, it is preferred that if the first cast, the further cast, or both, is increased by mechanical means, that the increase is less than 100%, in one embodiment less than 50%, further in one embodiment less than 20%, and particularly preferred less than 5%. E.g., the first wire has a first cast of 80 mm. A mechanical means is used to increase the first cast to 82 mm.

Cooling Means

In a one embodiment, the further wire is fed through a cooling means. It is preferred in one embodiment that the cooling means includes a coolant. In this embodiment it is further preferred that the coolant has a temperature in the range of 15° C. to 35° C., in one embodiment 18° C. to 30° C., and further in one embodiment 22° C. to 27° C. In this embodiment it is also preferred that the coolant is a gas, in one embodiment an inert gas. In this embodiment it is preferred that the further wire is cooled by circulating the gas through the cooling means, in one embodiment using a gas flow without a fan.

Cleaning the First Wire

The first wire is cleaned using an alkaline solution and ultrasonic sound. After cleaning, the first wire is first rinsed with distilled water, and then wiped with isopropyl alcohol. The first wire is then air dried. Such a cleaning method is well-known to a person skilled in the art.

Wire Segment

In one embodiment, at least one wire segment is obtained from the further wire. A "wire segment" is defined as a segment of the further wire that has been separated from the further wire. It is preferred to separate the wire segment by cutting the further wire. In one embodiment, it is preferred that the further wire is cut using at least one of the following; a blade, a laser, a shearing means.

It is preferred in one embodiment that the wire segment includes at least one outer layer. It is preferred that the at least one outer layer is a first outer layer. In this embodiment it is preferred that the first outer layer includes an organic material, in one embodiment a polymer, and further in one embodiment a material selected from the group consisting of polyurethane, polyimide, polytetrafluoroethylene, perfluoro alkoxy alkanes, ethylene tetrafluoroethylene, or a combination of two or more thereof. In this embodiment it is also preferred that he first outer layer is electrically insulating.

It is also preferred in one embodiment that the at least one outer layer is a further outer layer. In this embodiment it is preferred that the further outer layer includes at least one metal, in one embodiment silver, at least one a metal compound, in one embodiment silver chloride, or a combination thereof. It is preferred that the further outer layer is electrically conducting.

It is preferred in one embodiment that the wire segment includes the first outer layer and the further outer layer. It is also particularly preferred that wire segment includes the following layers: the first core layer, the further core layer, the first outer layer, the further outer layer.

Grains

In the context of one embodiment, grains are crystals which are present in the first wire, the further wire, or both. It is preferred in one embodiment that a first volume of the first wire includes of at least 70%, in one embodiment at least 80%, further in one embodiment at least 90%, and particularly in one embodiment at least 95% grains. Here the first volume is defined as the volume of a first longitudinal portion of the first wire, wherein the first longitudinal portion has a length that is at least 10% of the total length of the first wire. It is preferred in one embodiment that a further volume of the further wire includes of at least 70%, in one embodiment at least 80%, further in one embodiment at least 90%, and particularly in one embodiment at least 95% grains. Here the further volume is defined as the volume of a further longitudinal portion of the further wire, wherein the further longitudinal portion has a length that is at least 10% of the total length of the further wire.

There is, often but not always, no preferred orientation of the grains, e.g., the grains can be random with no preferred direction, the grains can be directed, or a combination thereof. An example of the latter orientation is the following: 50% of the grains are directed, while the other 50% of the grains are randomly orientated. It is preferred in one embodiment that a grain includes a grain boundary. In this embodiment it is preferred that the grain boundary defines a volume or a surface area of the grain. It is also preferred that a grain boundary is at least partially formed where at least two grains meet. There is no preferred geometrical form of the grains, e.g., the grain forms can be irregular, or the grains can, to a first approximation, be in the form of a polygon.

FIG. 1 is a flowchart illustrating the comprising steps of a method 100, according to the embodiment, for producing the further wire. In step 101, a first wire is provided. In the optional step 102, the first wire is optionally arranged on a winch (at least one pay-out means). In step 103 the first wire is fed through a furnace to obtain a further wire.

Figure 2:
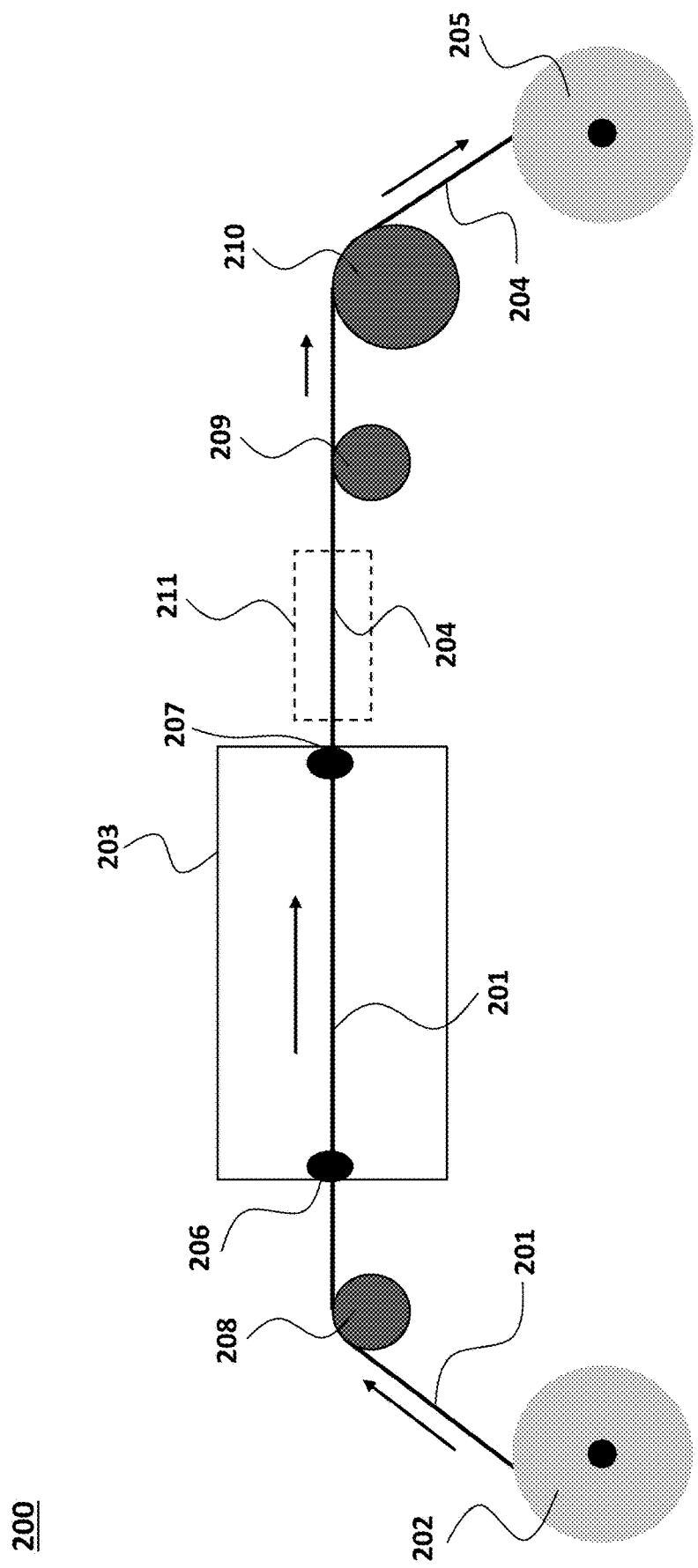
FIG. 2: schematic illustration of a device, according to the embodiment, that is used for producing the further wire.

FIG. 2 illustrates a schematic illustration of a device 200, according to one embodiment, used for producing a further wire 204. A first wire 201 is arranged on a pay-out means 202 that includes a first winch. The first wire 201 is paid out and fed through a furnace 203. The further wire 204 is defined as any section of the first wire 201 that has exited the furnace 203. The further wire 204 is taken up by a take-up means 205 that includes a further winch. In FIG. 2, the first wire 201 enters the furnace 203 through the furnace inlet 206 and exits the furnace 203 through the furnace outlet 207. The arrows in FIG. 2 indicate the direction of motion of the first wire 201 and the further wire 204.

FIG. 2 also illustrates that the production device has a tension control means 208, a support means 209, and a guidance means 210. All of the aforementioned means comprise a pulley. The first wire 201 passes over the tension control means 208, thereby allowing a first tension in the first wire 201 to be controlled. Due to arrangement of the first wire 201 on the pay-out means 202 and the arrangement of the further wire 204 on the take-up means 205, a further tension in the further wire 204 is equal to the first tension in the first wire 201. The further wire 204 passes over the support means 209 and the guidance means 210. The production device 200 also has a cooling means 211 that the further wire 204 passes through. The support means 209 is used to prevent the further wire 204 from touching the sides of the cooling means 211.

Figure 3:
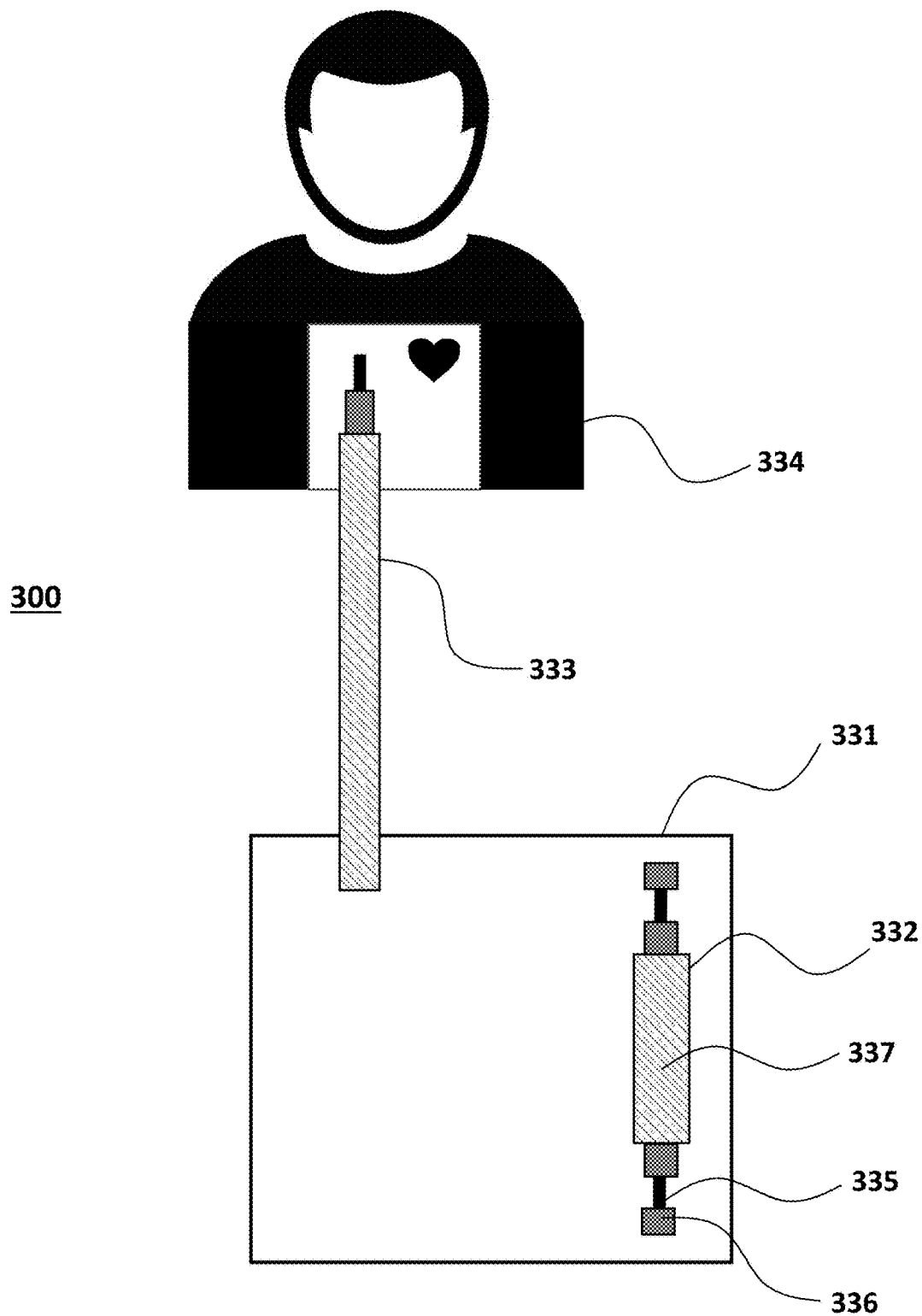
FIG. 3: schematic illustration of a use of wire segments, according to the embodiment, in a medical device.

FIG. 3 illustrates a use of wire segments, according to one embodiment, in a medical device 300. The medical device has a main body 331. A first wire segment 332 is used in the circuits of the main body 331. A further wire segment 333 is used as an electrode of the medical device 300. The medical device 300 is used to measure the blood glucose levels of a patient 334. Both the first wire segment 332 and the further wire segment 333 have a core layer 335, a first outer layer 336, and a further outer layer 337. The core layer 335 includes a first core layer that is surrounded by a further core layer.

The wire segments in FIG. 3 are produced by coating a further wire comprising the core layer 335 with the first outer layer 336, in order to obtain a first coated wire. The first coated wire is then coated with the further outer layer 337 to obtain a further coated wire. The first outer layer 336 and the further outer layer 337 are then selectively removed along the length of the further coated wire according to the patterns of the wire segments 332 and 333.

FIGS. 4A-4C illustrates how the cast of the wire should be measured 400. A longitudinal section of a wire is cut off to obtain a segment of the wire 440. The wire segment 440 is placed on a flat surface. Note that the wire segment 440 is viewed from above in FIGS. 4A-4C.

FIG. 4A illustrates how the cast of the wire should be measured if the wire segment 440 forms a loop. Wires with a cast of less than 300 mm generally fall into this category. Note that the endpoints of the wire segment 440 does not need to touch in order to form a loop, as shown in FIG. 4A-I. The cast is measured at the smallest possible diameter C of the loop, as shown in FIGS. 4A-I and 4A-II. The measured value of C is defined as the cast.

Wire segments obtained from wires with sufficiently large cast will not form a loop when placed on a flat surface. In this case, FIG. 4B illustrates how the cast is measured. A number of evenly spaced, imaginary points 441 are defined on the wire segment 440. The number of points 441 should be at least five. An imaginary circle 442 is fitted through these points 441. The diameter C of the imaginary circle defines the cast of the wire.

FIG. 4C is an illustration of how a loop of a wire segment is defined. The wire segment 440 has two endpoints A and B. Choose a point D in the position as shown in FIG. 4C. Next, starting from point A, move along the wire segment 440 to the point B. As one moves along the wire segment 440, one will trace an angle θ, as shown in FIG. 4C. The number of loops that the wire segment forms is given by θ/360°. E.g., if θ=360°, then the number of loops is 360°/360°, i.e., the wire segment forms one loop. If θ=450°, then the number of loops is 450°/360°, i.e., the wire segment forms 1.25 loops. E.g., in FIG. 4A-I, θ>360°.

Figure 5A:
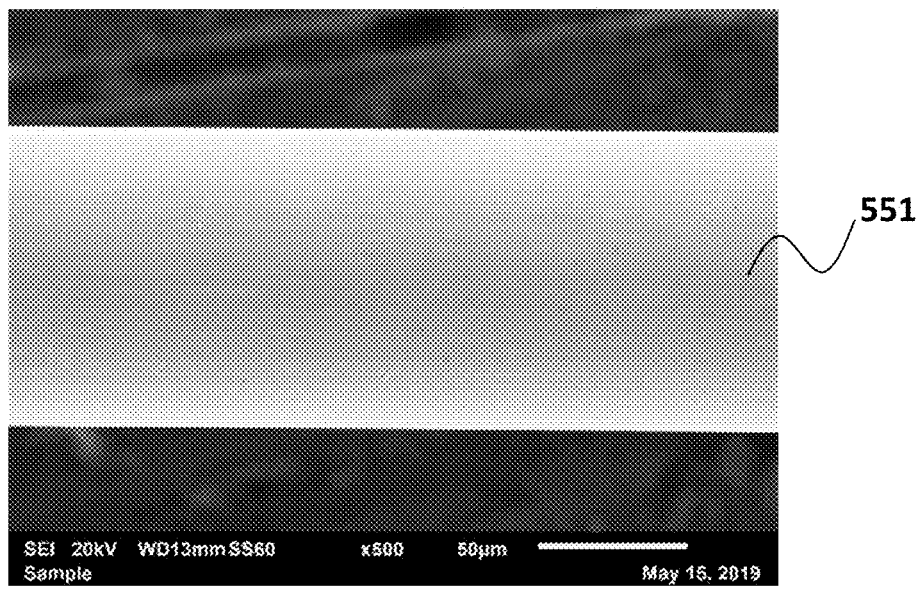
FIGS. 5A-5B: SEM images of surfaces of further wires.
Figure 5B:
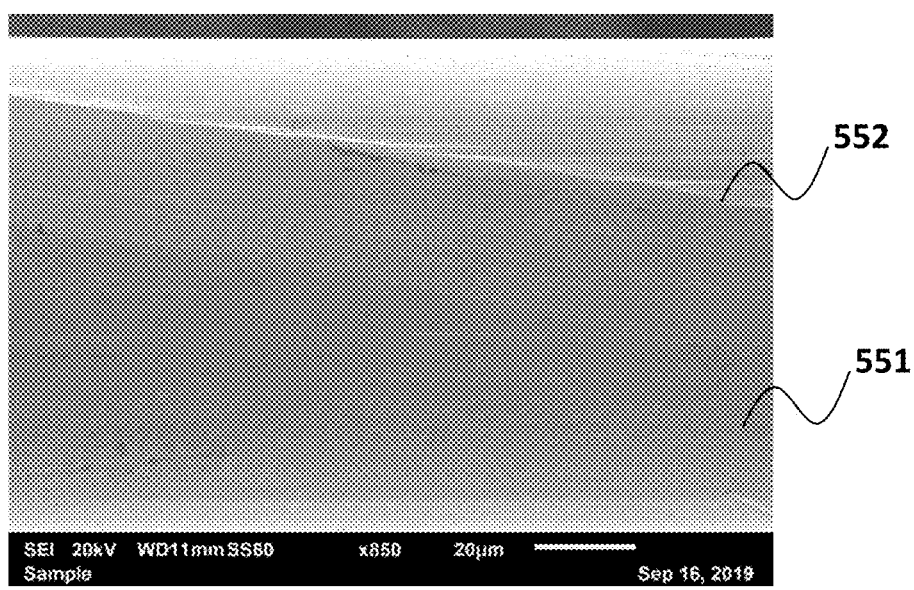

FIGS. 5A-5B show scanning electron microscope images 500 of surfaces of further wires. FIG. 5A illustrates a surface of a further wire 551 that was produced according to a method of the present embodiment. No mechanical means were used to increase the cast of the wire. It can be seen that the surface of the further wire 551 is free of defects. FIG. 5B illustrates a surface of a further wire 551, wherein the further wire 551 was produced using a method that is not according to the present embodiment. In FIG. 5B, a mechanical means was used to increase the cast of the wire. Using the mechanical means leads to the formation of shearing marks 552 on the surface of the further wire 551. Furthermore, the shearing marks 552 are not only confined to the surface of the further wire 551, but also extend (not shown in FIG. 5B) into the body of the further wire 551. Straightening by a mechanical means produces residual stresses that lead to subsequent stress relaxation and creep, thereby decreasing the cast of the further wire.

Figure 6A:
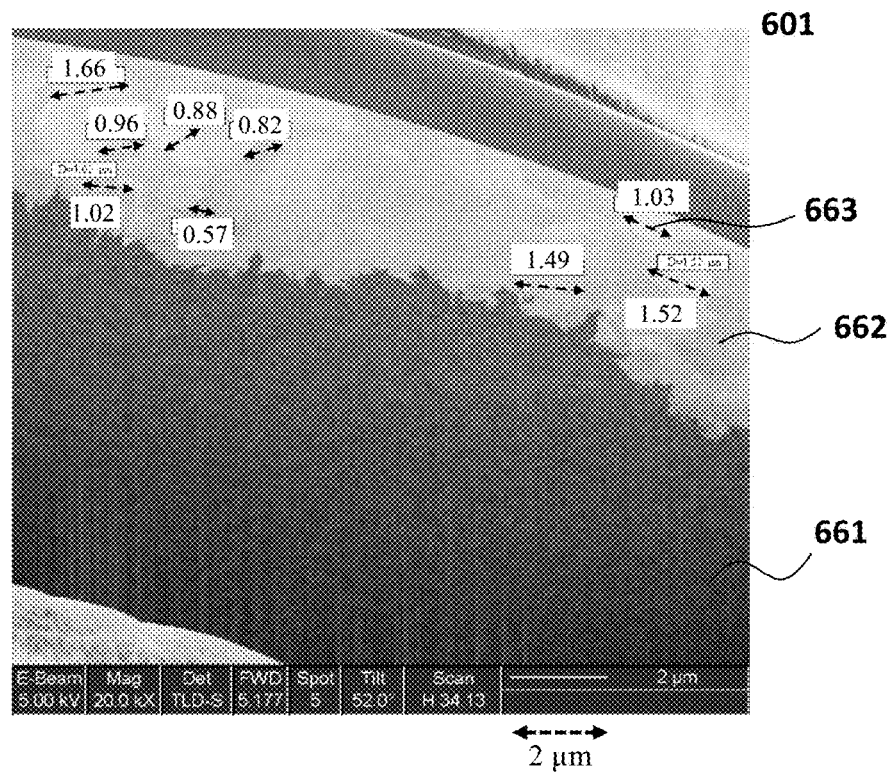
FIGS. 6A-6D: SEM images of cross-sections of a first wire and a further wire, produced according to a method of the embodiment.
Figure 6B:
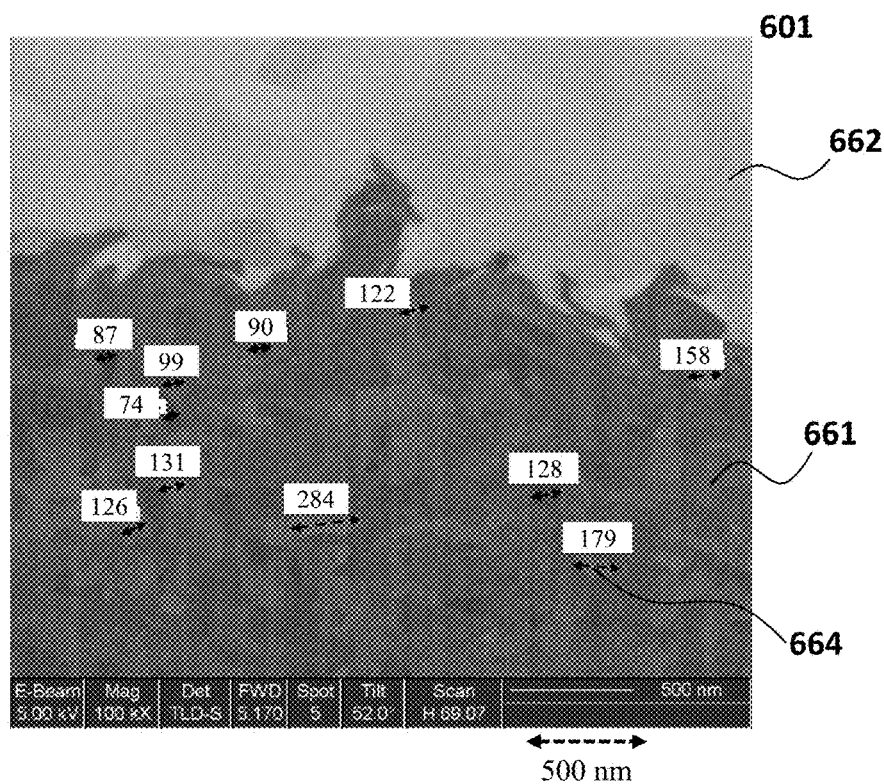
Figure 6C:
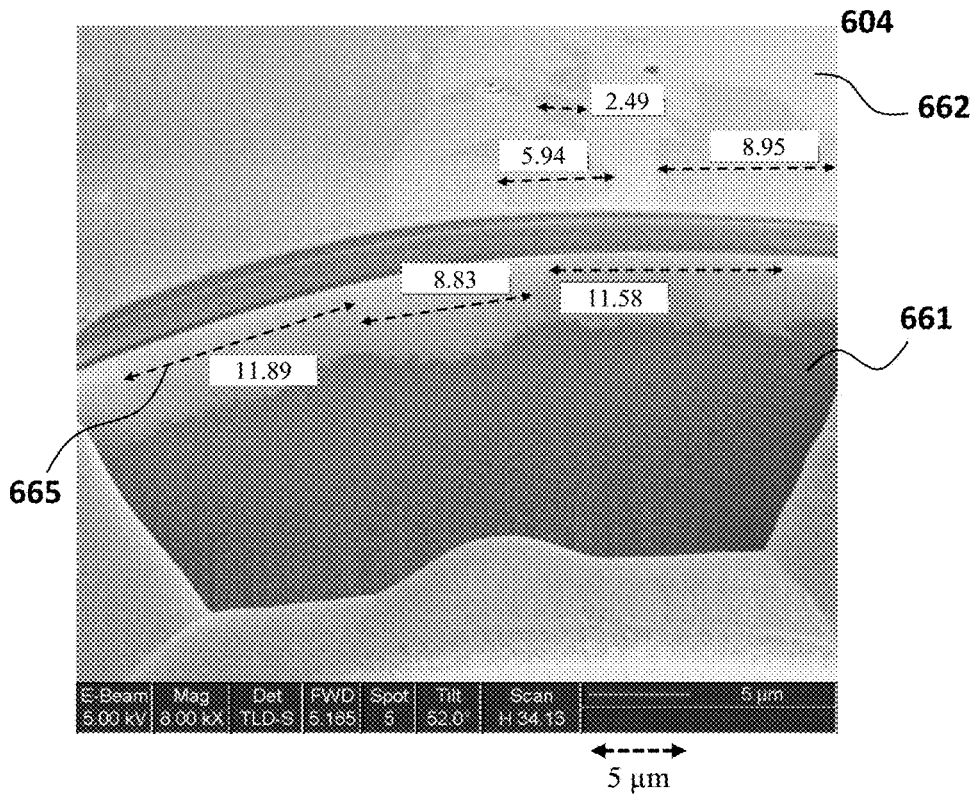
Figure 6D:
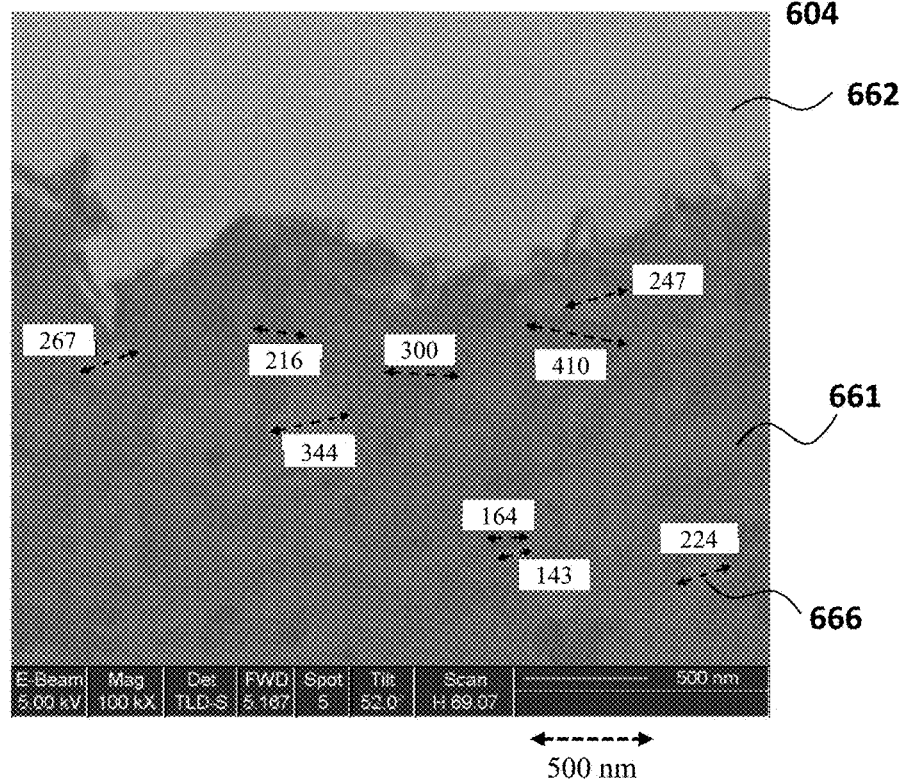

FIGS. 6A-6D show scanning electron microscope images taken of cross-sections 600 of a first wire 601 and a further wire 604. The arrows and values below the images indicate the scale of the images. The further wire 604 was produced according to a method of the present embodiment, and without using a mechanical straightening means. Furthermore, the cast of the further wire 604 is larger than the cast of the first wire 601. Both the first wire 601 and the further wire 604 have a tantalum core 661 surrounded by a platinum cladding 662. FIG. 6A illustrates sizes (indicated by the dashed arrows) of grains, e.g., 663, in the platinum cladding 662 of the first wire 601. The values indicated on the image are the sizes of the grains in mm. The sizes of the grains are between 0.5 mm to 1.7 mm. FIG. 6B illustrates sizes (indicated by the dashed arrows) of grains, e.g., 664, in the tantalum core 661 of the first wire 601. The values indicated on the image are the sizes of the grains in nm. The sizes of the grains are between 60 nm to 290 nm. FIG. 6C illustrates sizes (indicated by the dashed arrows) of grains, e.g., 665, in the platinum cladding 662 of the further wire 604. The values indicated on the image are the sizes of the grains in mm. The sizes of the grains are between 2.5 mm to 12.5 mm. FIG. 6D illustrates sizes (indicated by the dashed arrows) of grains, e.g., 666, in the tantalum core 661 of the further wire 604. The values indicated on the image are the sizes of the grains in nm. The sizes of the grains are between 170 nm to 430 nm. The formation of new grains, as well as the increase in grain sizes of the further wire 604, compared to the grain sizes of the first wire 601, leads to a reduction in surfaces stresses in the wire, as well as in increase in the cast of a wire.

Test Methods

Unless otherwise stated, all test methods are performed at a temperature of 25° C. and a pressure of 101 325 Pa.

Wire Cast

An unconstrained segment of a wire is placed on a flat and smooth surface. A length of the wire segment is chosen so that the wire segment forms 1.25 loops. The wire segment is unconstrained in the sense that there is no device or person holding the wire segment.

If the wire segment forms a loop, the cast is measured as explained in FIG. 4a. The cast is measured using a calibrated ruler. Such rulers are well-known to a person skilled in the art. If the wire segment does not form a complete loop, the cast is measured as explained in FIG. 4b. For this measurement, the wire is placed under an inspection system. The inspection system that is used in the present embodiment is the SmartScope system commercially available from Optical Gaging Products, United States of America. Twenty evenly spaced points are chosen along a length of the wire, and the SmartScope software is used to fit an imaginary circle through these points. The diameter of the imaginary circle is defined as the cast of the wire.

Temperature

The furnace temperature is measured at three positions in the furnace using a thermal couple. If L is the length of the furnace, the positions are measured at 0.15L, 0.5L, and 0.85L. In other words, the temperature is measured at the centre of the furnace, as well as near the furnace inlet and the furnace outlet. The furnace temperature is defined as the average of the three measurements.

The melting temperature of materials are well-known to a person skilled in the art. These can be found in, e.g., Engineering ToolBox, (2005). *Metals and Alloys—Melting Temperatures*. [online] Available at: www.engineeringtoolbox.com/melting-temperature-metals-d_860.html [Accessed 21 Nov. 2019].

The recrystallisation temperatures of materials are well-known to a person skilled in the art. These can be found in e.g., *Encyclopedia of Materials: Science and Technology*. Cahn et al. (eds.), (2005), Elsevier.

Ultimate Tensile Strength

Ultimate tensile strength is measured according to the standard ASTM 8E. For the testing procedure, the following is used: the test speed is 0.013 m/min, the gauge length of the wire is 0.25 m, and the tensile force is measured with a 50N load cell.

Wire Tension

Wire tension is measured using a hand-held tension gauge. Suitable tension gauges are well-known to a person skilled in the art.

Grain Size

To measure the grain size of a wire (the first wire or the further wire), a first crosssection is made of the wire using a focused ion beam (FIB). The grain size of the first crosssection is then measured using a scanning electron microscope (SEM). The SEM is used to generate a two-dimensional first image of the grain structure of a wire. The FIB used is a DA300 dual beam FIB commercially available from FEI Company. The SEM used is a JSM7800FLV high-resolution, field emission, scanning electron microscope (HR-FESEM) commercially available from JEOL Ltd, Japan.

The sizes of 200 grains are measured. If the first image contains less than 200 grains, then a further image is generated by making a further cross-section of the wire. This process is repeated until the combined number of grains in all the images is 200. The average grain size is calculated by taking the arithmetic mean of the 200 grain size measurements.

Using the two-dimensional image (e.g., the first image, the further image), the size of a grain is defined as the maximum, straight-line distance that can be measured between any two points on the grain boundary. E.g., if the grain is elongated, the grain size should be measured along the direction of elongation. Furthermore, the grain boundary could have a non-negligible thickness. When measuring the grain size, the grain size should not include the thickness of the grain boundary.

Diameter

The diameter of a wire is measured according to the standard IEC 60851-2:2009.

Length

Length is measured according to the standard ISO 3611: 2010.

Electrical Conductivity

Electrical conductivity is measured according to the standard ASTM B193-16.

Young's Modulus

Young's modulus is measured according to the standard ASTM E111-17.

Consistency of Wire Segments

Wire segments are obtained from the further wire. These wire segments are used as electrodes in continuous glucose monitors (CGM) that measure glucose levels. The consistency of the wire segments is measured as follows: 100 CGM are used, in turn, to measure the glucose levels of a standard sample. Every CGM is used to make 200 measurements. The variance of the measurements is an indication of the measurement consistency. The smaller the variance, the more reliable a CGM is.

Noise Level of Wire Segments

Noise levels can be measured as described in Measurement of very-low frequency noise, J. Lopez de la Fuente (1970), Technische Hogeschool Eindhoven, DOI 10.6100/IR94820:

EXAMPLES

The following applies to Examples 1-3: every example consists of repeating an experiment multiple times, with several parameters varied between experimental repetitions. Furthermore, every experimental repetition is performed using three samples of the first wire.

The following applies to all experimental repetitions: the first wire has a first core layer with a diameter of 100 μm. The first core layer includes tantalum. The first core layer is surrounded by a further core layer that has an average thickness of 4 μm. The further core layer includes platinum.

Note that the melting temperature and recrystallisation temperature of tantalum is 3017° C. and 900° C., respectively. For platinum, the melting temperature and recrystallisation temperature is 1768° C. and 550° C., respectively.

The following also applies to all experimental repetitions: the first wire is fed through a furnace to obtain a sample of a further wire. Every section of the first wire remains in the furnace for 6 sec. A length of the furnace is 1.5 m. The furnace that is used for the examples is commercially available from Nabertherm GmbH, Germany.

Note that in the results shown in the examples, a further wire is defined as being straight if the cast is larger than 10 000 mm. If the further wire is "waved", this means that the wire is neither straight, nor has a uniquely measurable further cast. A further wire that is "waved" is e.g., to a first approximation, in the form of a sinusoidal wave.

Example 1

The example includes performing the same experiment under similar conditions, with the exception that the temperature of the furnace is varied between the experimental repetitions. The furnace temperatures used for the experimental repetitions are shown in Table 1.

For each of the experimental repetitions, the following applies: three samples of the first wire with varying cast are provided, as shown in Table 1. The samples of the first wire are separately fed through the furnace at a speed of 15 m/min to obtain three samples of the further wire. A first tension in the first wire and a further tension in the further wire of all three samples are kept constant at 110 g. The properties of the three samples of the further wire are also shown in Table 1.

TABLE 1 experimental results of Example 1.

| Furnace temperature (° C.) | Wire | Sample | Cast (mm) |
|---|---|---|---|
| Provided first wire | First | 1 | 80 |
| | First | 2 | 84 |
| | First | 3 | 85 |

TABLE 1-continued experimental results of Example 1.

| Furnace temperature (° C.) | Wire | Sample | Cast (mm) |
|---|---|---|---|
| 500 | Further | 1 | 75 |
|  | Further | 2 | 75 |
|  | Further | 3 | 80 |
| 600 | Further | 1 | 95 |
|  | Further | 2 | 90 |
|  | Further | 3 | 90 |
| 700 | Further | 1 | 135 |
|  | Further | 2 | 140 |
|  | Further | 3 | 135 |
| 800 | Further | 1 | 140 |
|  | Further | 2 | 140 |
|  | Further | 3 | 135 |
| 850 | Further | 1 | 175 |
|  | Further | 2 | 200 |
|  | Further | 3 | 280 |

Table 1 illustrates that for a furnace temperature of 500° C., the further cast of the further wire decreases. However, if the temperature of the furnace is 600° C. or higher, the further casts increases to values that lie in the range from 95 mm and 280 mm, i.e., the further cast of the further wires are larger than the first cast of the first wires.

Example 2

Example 2 is similar to Example 1, except for the following differences:
 a. the three samples of the first wire have a different cast;
 b. different furnace temperatures are used.

The range of furnace temperatures, as well as the cast of the three samples of first wire are shown in Table 2. Also shown is the three samples of the further wire that are obtained.

TABLE 2 experimental results of Example 2.

| Furnace temperature (° C.) | Wire | Sample | Cast (mm) |
|---|---|---|---|
| Provided first wire | First | 1 | 162 |
|  | First | 2 | 180 |
|  | First | 3 | 210 |
| 400 | Further | 1 | Waved |
|  | Further | 2 | Waved |
|  | Further | 3 | Waved |
| 450 | Further | 1 | Waved |
|  | Further | 2 | Waved |
|  | Further | 3 | Waved |
| 500 | Further | 1 | Waved |
|  | Further | 2 | Waved |
|  | Further | 3 | Waved |
| 550 | Further | 1 | Waved |
|  | Further | 2 | Waved |
|  | Further | 3 | Waved |
| 600 | Further | 1 | Straight |
|  | Further | 2 | Straight |
|  | Further | 3 | Straight |
| 650 | Further | 1 | Straight |
|  | Further | 2 | Straight |
|  | Further | 3 | Straight |
| 700 | Further | 1 | Straight |
|  | Further | 2 | Straight |
|  | Further | 3 | Straight |
| 750 | Further | 1 | Straight |
|  | Further | 2 | Straight |
|  | Further | 3 | Straight |
| 800 | Further | 1 | Straight |
|  | Further | 2 | Straight |
|  | Further | 3 | Straight |

Example 3

Example 3 is similar to Example 2, except that the samples of the first wire are separately fed through the furnace at a speed of 10 m/min. The three samples of the further wire that are obtained are shown in Table 3.

In addition, the average first grain size of the first wire and the average further grain size of the further wire were also measured. For the first wire, the average first grain size of the first core layer (comprising tantalum) is in the range of 70 nm to 280 nm. Furthermore, the average first grain size of the further core layer (comprising platinum) is in the range of 0.6 μm to 1.6 μm. By contrast, for the further wire, the average further grain size of the first core layer is in the range of 180 nm to 420 nm. Furthermore, the average further grain size of the further core layer is in the range of 3 μm to 12 μm.

TABLE 3 experimental results of Example 3.

| Furnace temperature (° C.) | Wire | Sample | Cast (mm) |
|---|---|---|---|
| Provided first wire | First | 1 | 162 |
|  | First | 2 | 180 |
|  | First | 3 | 210 |
| 400 | Further | 1 | Waved |
|  | Further | 2 | Waved |
|  | Further | 3 | Waved |
| 450 | Further | 1 | Waved |
|  | Further | 2 | Waved |
|  | Further | 3 | Waved |
| 500 | Further | 1 | Waved |
|  | Further | 2 | Waved |
|  | Further | 3 | Waved |
| 550 | Further | 1 | Waved |
|  | Further | 2 | Waved |
|  | Further | 3 | Waved |
| 600 | Further | 1 | Straight |
|  | Further | 2 | Straight |
|  | Further | 3 | Straight |
| 650 | Further | 1 | Straight |
|  | Further | 2 | Straight |
|  | Further | 3 | Straight |
| 700 | Further | 1 | Straight |
|  | Further | 2 | Straight |
|  | Further | 3 | Straight |
| 750 | Further | 1 | Straight |
|  | Further | 2 | Straight |
|  | Further | 3 | Straight |
| 800 | Further | 1 | Straight |
|  | Further | 2 | Straight |
|  | Further | 3 | Straight |

Tables 2 and 3 show that for the first wire with a first cast between 162 mm and 220 mm, it is possible to obtain the further wire that is straight, i.e., the further cast is more than 10 000 mm. Tables 1 to 3 show that when the temperature of the furnace is 600° C., or higher, this leads to the further cast of the further wire being larger than the first cast of the first wire.

The present embodiment can therefore be used to obtain further wires that are straight, even if the first cast is small (as in Example 1). If the further cast is not sufficiently larger than the first cast, the further wire can be fed through the furnace multiple times until the further wire is straight.

Example 4

In this example, the method of the present embodiment is compared to two methods that form part of the prior art. The first method is disclosed in CN208667797U, wherein the first wire is fed through an annealing furnace. Although superficially similar to the present embodiment, the device disclosed in CN208667797U straightens the first wire by varying the first tension in the first wire and the further tension in the further wire.

While a second prior art document CN105154657A also discloses the feeding of the first wire through a furnace, the furnace is used for annealing, and nor for improving the cast of the further wire. For this purpose, two sets of rollers are used to straighten the first wire, prior to feeding the first wire through the furnace.

For the comparison, the method disclosed in the present embodiment is used to produce 100 samples of the further wire. The first wire used to produce the further wire is as described in the preceding experiments, with the following value fixed: the samples of the first wire have an average first cast of 162 mm. The first cast of a sample of the first wire does not vary by more than 5% from the average value of the first cast. For the method of the present embodiment, the further wires are obtained using the same set-up as in Example 2, with the average temperature of the furnace being 700° C.

TABLE 4 advantages that the method of the present embodiment has over the prior-art method.

| | Present embodiment | CN208667797U | CN105154657A |
|---|---|---|---|
| Diameter of first wire (mm) | 0.102 | 0.6 | 3 |
| Production efficiency (m/min) | 15 | Unknown | 10-20 |
| Damage to further wire | None | Breakage | Scratches |
| Variation in diameter of further wire | 2% | >2% | >2% |
| Cast increase between first wire and further wire (%) | >300% | Only some straightening | Only some straightening |
| Production cost ($/m) | Least | More | Most |
| Downtime (h) | Least | More | Most |
| Set-up time | Least | Most | More |
| Consistency of wire segments | High | Wire segments not produced | Wire segments not produced |
| Noise level of wire segments | Very low | Wire segments not produced | Wire segments not produced |

The fields in Table 4 are as follows:
Diameter of first wire: the average diameter of the first wire.
Production efficiency: the speed at which the further wire is produced.
Damage to further wire: damages resulting from the production method used.
Variation in diameter of further wire: the average diameter of the further wire compared to the average diameter of the first wire.
Production cost: the cost to produce 1 m of the further wire.
Downtime: the downtime of production equipment for maintenance or as a result of the production equipment breaking.
Set-up time: the time needed to set-up the first wire in order to start feeding the first wire through the furnace. E.g., arranging the first wire on a pay-out means.
Consistency of wire segments: wire segments produced from the further wire are used as sensors in medical devices used for measurement. The consistency indicates how the measurements differ between the medical devices when measuring the same sample.
Noise level of wire segments: wire segments produced from the further wire are used as sensors in medical devices used for measurement. The wire segments will have an intrinsic noise level that will affect measurements. This noise level scales inversely with frequency It is clear from the above table that the present embodiment provides an improvement over the prior art for the production of the further wire. Furthermore, the present embodiment also leads to an improvement in the wire segments that can be obtained from the further wire. Therefore, if the further cast of the further wire is straight, or larger than the first cast of the first wire, this improves downstream processes, such as producing wire segments, as well as the quality of the wire segments that are obtained.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein. Therefore, it is intended that this disclosure be limited only by the claims and the equivalents thereof.

The invention claimed is:

1. A method for producing a further wire, wherein the method comprises:
a. providing a first wire;
b. feeding the first wire through a furnace to obtain the further wire;
wherein
a further cast of the further wire is larger than a first cast of the first wire,
a temperature of the furnace is in the range of 500° C. to 950° C., and
a first section of the first wire has a residence time in the furnace that is in the range of 0.5 sec to 40 sec;
wherein an average further grain size of crystals in the further wire is larger than an average first grain size of crystals in the first wire by at least 50%.

2. The method according to claim 1, wherein the further cast of the further wire is larger than the first cast of the first wire by at least 150%.

3. The method according to claim 1, wherein the speed of feeding the first wire through the furnace is in the range of 2 m/min to 22 m/min.

4. The method according to claim 1, wherein a tension on the first wire is in the range of 70 g to 200 g.

5. The method according to claim 1, wherein the first wire, the further wire, or both, comprises a metal or a metal alloy.

6. The method according to claim 1, wherein at least one or all of the following applies to the further wire:
  a. a further cast that is larger than 300 mm;
  b. comprises a first core layer, wherein an average further grain size of the first core layer is in the range of 130 nm to 480 nm;
  c. comprises a further core layer, wherein an average further grain size of the further core layer is in the range of 0.6 μm to 20 μm;
  d. has a further ultimate tensile strength that is in the range of 1200 MPa to 2000 MPa.

7. The method according to claim 1, wherein at least one or all of the following applies to the first wire:
  a. a first cast that is in the range of 20 mm to 300 mm;
  b. comprises a first core layer, wherein an average first grain size of the first core layer is in the range of 20 nm to 400 nm;
  c. comprises a further core layer, wherein an average first grain size of the further core layer is in the range of 0.1 μm to 10 μm;
  d. has a first ultimate tensile strength that is in the range of 1000 MPa to 1800 MPa.

8. The method according to claim 1, wherein at least one or all of the following applies to the first wire, the further wire, or both:
  a. a length in the range of 1000 m to 12000 m;
  b. a diameter in the range of 40 μm to 160 μm;
  c. an electrical conductivity in the range of $10^4$ S/m to $10^8$ S/m;
  d. a Young's modulus in the range of 10 GPa to 300 GPa.

* * * * *